United States Patent

Carver et al.

[11] Patent Number: 5,380,664
[45] Date of Patent: * Jan. 10, 1995

[54] HEMATOLOGY CONTROL COMPOSITIONS FOR THREE POPULATIONS OF LEUKOCYTES; AND METHODS FOR THEIR PREPARATION AND USE IN WHOLE BLOOD CONTROL SYSTEMS

[75] Inventors: Franklin J. Carver, Miami; Theodore J. Gerula, Miami Lakes, both of Fla.

[73] Assignee: Coulter Corporation, Miami, Fla.

[*] Notice: The portion of the term of this patent subsequent to Nov. 3, 2004 has been disclaimed.

[21] Appl. No.: 510,376

[22] Filed: Apr. 17, 1990

Related U.S. Application Data

[60] Continuation of Ser. No. 355,047, May 16, 1989, abandoned, which is a continuation of Ser. No. 115,671, Nov. 2, 1987, abandoned, which is a division of Ser. No. 612,091, May 18, 1984, Pat. No. 4,704,364.

[51] Int. Cl.$^6$ ............................................. G01N 19/00
[52] U.S. Cl. ........................................ 436/10; 436/15; 436/16; 436/17; 436/18; 435/2
[58] Field of Search ................................ 436/8–19; 435/2; 424/3; 252/408.1

[56] References Cited

U.S. PATENT DOCUMENTS

| | | | |
|---|---|---|---|
| 3,574,137 | 4/1971 | Decasperis | 252/408.1 |
| 3,873,467 | 3/1975 | Hunt | 436/18 |
| 3,973,913 | 8/1976 | Louderback | 436/10 |
| 4,250,051 | 2/1981 | Armstrong | 436/18 |
| 4,264,470 | 4/1981 | Chestain et al. | 252/408.1 |
| 4,405,719 | 9/1983 | Crews et al. | 436/10 |
| 4,485,175 | 11/1984 | Ledis et al. | 436/17 |
| 4,575,490 | 3/1986 | Ornstein et al. | 436/10 |

*Primary Examiner*—James C. Housel
*Assistant Examiner*—N. Bhat
*Attorney, Agent, or Firm*—Mitchell E. Alter

[57] ABSTRACT

This invention primarily is directed to a hematology reference control solution, the three separate white cell control portions thereof consisting of three types of fixed red cells of determined size distribution for checking the operation of a particle analyzing instrument, including its predetermined lower and upper threshold settings for each class or subclass of leukocytes.

For preparing a human granulocyte analogue, nurse shark erythrocytes are altered and fixed in a chilled solution to simulate in number, size and distribution the granulocytes in human whole blood.

Such a granulocyte analogue is useful as a free-standing reference control, for determination of human granulocytes only, or can be comingled with reference controls for lymphocytes and mononuclear cells for use with multi-parameter instruments to give a trimodal leukocyte reference control, which itself can be included in a multiple-analysis hematology reference control, having components for also determining red blood cell and platelet parameters.

12 Claims, 1 Drawing Sheet

HEMATOLOGY CONTROL COMPOSITIONS FOR THREE POPULATIONS OF LEUKOCYTES; AND METHODS FOR THEIR PREPARATION AND USE IN WHOLE BLOOD CONTROL SYSTEMS

This application is a continuation of application Ser. No. 07/355,047 filed May 16, 1989 now abandoned, which is a continuation of abandoned Ser. No. 07/115,671 filed Nov. 2, 1987 which is a division of Ser. No. 06/612,091 filed May 18, 1984, now U.S. Pat. No. 4,704,364, issued Nov. 3, 1987.

BACKGROUND OF THE INVENTION

This invention relates to hematology control compositions, and methods for their use in a reference standard for particle analysis instrumentation of the COULTER ® type. More particularly, this invention relates to a three-component system for simulating the three major components of human leukocytes, namely lymphocytes, mononuclear cells and granulocytes, and optionally sub-divisions thereof, which is compatible with known red blood cell and platelet controls.

Mononuclear cells are single nucleated blood cells which include monocytes and numerous mature and immature forms of lymphocytes and immature myelocytes and erythrocytic blood cells. The modified COULTER COUNTER Model S Plus can delineates mature lymphocytes and polymorphic granulocytes from the general group of mononuclear cells found in circulating blood under normal and pathological conditions. These circulating mononuclear blood cells include promyelocytes, myelocytes and blast cells as well as monocytes. Since monocytes are the most prevalent mononuclear cell population under normal hemopoietic conditions, the 90 to 160 fL region can be referred to as the monocyte region.

The use of electronic particle counters in hematology is well known. U.S. Pat. No. 2,656,508 discloses a basic apparatus utilizing the Coulter principle for this purpose. U.S. Pat. No. 3,757,213 contains a description of several such devices which incorporate threshold circuitry. Threshold circuitry excludes random amplitude signals caused by noise and background debris of inconsequential particles in the suspension. It may also be used to limit the size range of the particles counted. Adjustable threshold circuits with dials marked off in mathematically related dial settings are in common use.

Although this disclosure will be directed primarily to embodiments involving the use of electronic particle counters of the COULTER type, it should be understood that the particle controls herein disclosed, and their methods of use described herein, find wide application with particle counters generally. Accordingly, the term "electronic particle counter" should be understood to include, in addition to COULTER COUNTER ® instruments, any other type of particle counter which discriminates between particles of various sizes by the use of electronic discriminator circuits ("thresholds") which respond electronically to signals indicative of particle size, mass or particle volume. COULTER and COULTER COUNTER are Registered Trademarks of Coulter Electronics, Inc.

Calibration check techniques for red blood cell (erythrocyte), white blood cell (leukocyte) and platelet (thrombocyte) counts and physical attributes are well developed. The material used for checking calibration, hereinafter called a control, also can be used to calibrate a hematology instrument. The techniques for using a control generally involve counting known populations of particles suspended in a liquid vehicle in the control preparation, which usually is diluted substantially with a diluent prior to counting. Heretofore, however, no control had been developed for use with three subgroups of leukocytes, namely, lymphocytes, mononuclear cells and granulocytes, since the equipment for automatic counting of these sub-groups had not been developed.

It is evident that a control product must accurately indicate on a comparative basis what a test sample of fresh blood constitutes with regard to the determinations in question. It is further evident how important it is for the control product to simulate fresh blood, since blood components, such as red blood cells, can hemolyze slowly and undergo changes in size and shape within hours after removal from a blood donor. Similarly, white blood cells suffer degenerative changes.

Quality control long has been a necessary and routine procedure in clinical hematology. Accuracy in the counting of red and white blood cells and in the making of hematocrit and hemoglobin determinations of the patient's serum is dependent, in part, upon the use of adequate control standards. Thus, the accuracy of the manual technique of particle counting, such as by the classical method of microscopy, can be checked by giving the technician a so-called "blind" sample, or control standard, containing a known concentration of particles for comparison with the unknown samples for which determination has to be made. With the numerous types of automatic equipment for particle counting now available, quality control by the use of control standards is likewise necessary since the possibility of malfunctioning of the instrument is ever present. Consequently, the importance of accurate and reliable checks on hematological determinations that may be used in the diagnosis of disease is clear. The traditional method of maintaining a quality control program for automatic particle counting equipment has consisted of providing fresh human blood as a whole blood standard. However this fresh blood is usable for only one day. Consequently, durable blood products were developed which did not require fresh human blood.

In copending application Ser. No. 454,926, filed Jan. 3, 1983 now U.S. Pat. No. 4,485,175, an automatic method is described for differential determination of three populations of leukocytes using a COULTER COUNTER Model S Plus automated blood counter. Accordingly there is now a need for a reliable check of threshold calibration and additional operational performances for electronic particle counters typified by the COULTER COUNTER analyzers now marketed. Operators then can identify and document the volume ranges between which the three populations of leukocytes are to be counted routinely. There is further a need in the art for a reliable method for demonstrating instrument stability over a prolonged period of use.

Human lymphocytes, mononuclear cells and granulocytes have a specific size distribution range and after stabilization (for example with a fixative, such as formaldehyde), their responsiveness in diluents may not permit proper size discrimination. This would result in an inability to evaluate proper instrument operation. Both the upper and lower size limits for each population of leukocytes must be represented in the reference control material. In addition, the mean cell volume of each leukocyte population in the reference control material should be very close to that of normal human blood. When upper and lower size limits and mean cell volume are thus specified, it becomes a virtual necessity for the volume distribution histogram of the control material to approximate the normal distribution of the fresh human cells. This volume distribution must remain relatively constant regardless of the total white cell count and the range of ratios for all three populations representing abnormal low, normal and abnormal high conditions for human leukocytes. Therefore, it is necessary that the preservation process used in the manufacture of the reference control suspension does not cause significant shrinking or swelling of the cells. Also one must be sure that aging of the reference control does not result in deterioration of the volume distribution histogram characteristics or other parameters. A further requirement for the leukocyte component in a whole blood reference control for multi-parameter instruments is that the cells must not be completely lysed by the lytic reagent.

With the increasing use of automated devices capable of performing multiple hematological determinations and with the introduction of techniques of automated cell counting, the solution to the problem lies not in the pursuit of more effective ways of stabilizing "real" human leukocytes, but in substituting a surrogate which satisfies the specifications against which the product is made. Therefore, animal cells which could be converted into a useful control or calibrator were sought. Numerous citations to prior art are set forth with some explanation in this application. To the extent that further information regarding such prior art might be needed to more fully understand the herein invention, the following are incorporated by reference: U.S. Pat. Nos. 4,179,398; 4,213,876; 4,264,470; 4,299,726; 4,389,490; 4,405,719 and U.S. application Ser. No. 454,926, filed Jan. 3, 1983 now patent 4,485,175.

SUMMARY OF THE INVENTION

A novel feature of this invention is the preparation of a stable, reproducible hematology control for three populations of white blood cells. In the three-component leukocyte system of this invention, methods are given for preparing simulated lymphocytes from mammals, for example human erythrocytes, simulated mononuclear cells from avian, for example turkey erythrocytes, and simulated granulocytes from the erythrocytes of fishes, for example the nurse shark (Ginglymostoma cirratum). In addition, a novel method is included for the preparation of altered red blood cells of a predetermined size within limits, by control of the age of the red blood cell before treatment and the temperature and concentration of the fixing agent.

It has been discovered that the nurse shark (Ginglymostoma cirratum) has erythrocytes (red blood cells) that normally fall into a size range which is slightly larger than human granulocytes, and that these erythrocytes can be altered and fixed so as to be similar in volume distribution to the volume distribution of human granulocytes in whole blood, in order to be useful as a human granulocyte reference control. The granulocyte analogue so prepared is stable and reproducible for use as a stand alone reference control, or in trimodal white blood cell compositions which also contain altered and fixed turkey red blood cells to simulate human mononuclear cells, and altered and fixed human red blood cells to simulate human lymphocytes. The white blood cell analogues also can be included in a single multiple-analysis hematology reference control which determines not only white blood cell components, but also red blood cell and platelet parameters. The ratio and total cell count for the three leukocyte populations can be adjusted to represent pathological as well as normal conditions in human blood. These compositions are useful likewise in control and calibrator compositions particularly for automated particle analysis instruments employing the Coulter principle.

The cells treated by the methods disclosed herein and the compositions including such cells provide an excellent system of checks and balances so necessary in hematological determinations.

BRIEF DESCRIPTION OF THE DRAWINGS

FIG. 1A shows a histogram developed from a normal blood sample.

FIG. 1B shows a histogram developed from the hematology control system and method of the present invention.

Figure 1A:
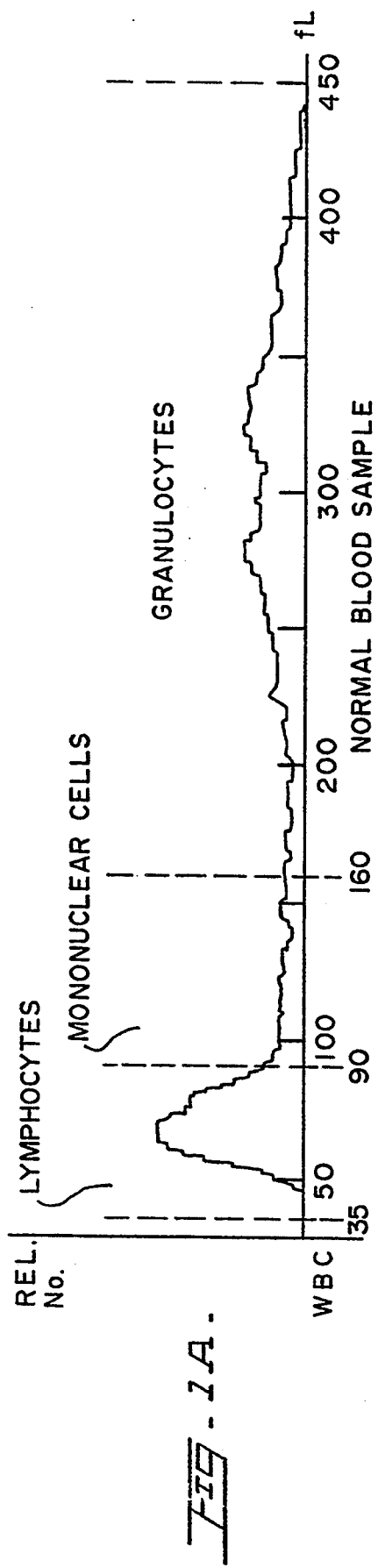
FIGS. 1A and 1B comparatively show the leukocyte distribution histograms of a sample made on the COULTER COUNTER Model S Plus automated blood cell counter.
Figure 1B:
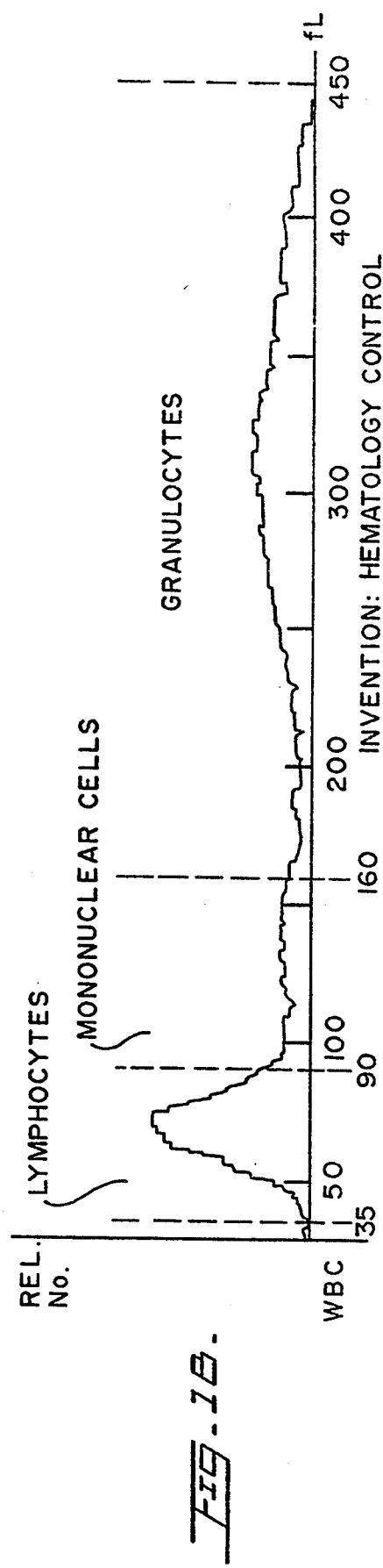

The invention has sufficient flexibility to allow the preparation of lymphocyte, mononuclear cell and granulocyte populations which may be larger or smaller than those shown in FIG. 1B. The changes in size then can reflect abnormal white blood cell size distributions, which are characteristic of human pathological conditions.

DETAILED DESCRIPTION OF THE INVENTION

Any system for automated differential counting of human leukocytes, which distinguishes three populations of leukocytes from other cells in the blood on the basis of characteristic size range and volume distribution, requires that the reference control material used as such closely simulate the size range and volume distribution characteristics of the respective cells in normal human blood. The problem is to find methods which accurately will produce cells of a given size in reproducible quantities sufficient to be available, as needed for use in controls for automated counting equipment.

Copending U.S. patent application Ser. No. 454,926, filed Jan. 3, 1983, now U.S. Pat. No. 4,485,175, describes a method and reagent system for three-volume differential determination of lymphocyte, mononuclear cell and granulocyte populations of leukocytes, using one type of a modified COULTER COUNTER Model S Plus instrument now sold as the Model S Plus IV diff and Model S Plus V. Following the procedure of this invention, the three classes of leukocytes are counted in femtoliters (fL) approximately as follows:

| | |
|---|---|
| lymphocytes | 35 to 90 ± 3 fL |
| mononuclear cells | 90 to 160 ± 3 fL |
| granulocytes | 160 to 450 ± 3 fL |

It is understood that the leukocytes which are classified and counted in the range designated as "mononuclear cells" include monocytes.

The procedure of this invention allows the treated red blood cells from different sources to match a plurality of threshold settings between about 25 fL and about 700 fL for many types of blood counting instruments. The other COULTER COUNTER instruments, with which this invention can be used, are of the Model S and Model S Plus types. The COULTER COUNTER Model S counts leukocytes from 25 fL to infinity. Other types of COULTER COUNTER Model S Plus instruments count lymphocytes from about 45 fL to about 99 fL and count mononuclear and granulocytes from about 99 fL to infinity.

Although methods are known for preparing control compositions for automatic counting instrumentation, where all leukocytes are counted as a single, whole population, no methods have been described for the preparation of blood cell controls for the differential counting of individual components of the leukocyte population. It is necessary to prepare an analogue for each of the major leukocyte components including lymphocytes, mononuclear cells and granulocytes in order to check the threshold settings of electronic particle counters.

Previously available reference control products for checking the performance characteristics of particle analysis instruments in whole blood controls were designed to evaluate total white cell count. The only requirement was a stable non-lysible component which had a majority of particles, above a minimum threshold, for example 35 to 45 fL. However, the current multiple white blood cell population analysis requires particles of specific size increments. Furthermore, there is a need for such a reference control which can be used over a long period of time without substantial change occurring in the reference values obtained therefrom.

U.S. Pat. No. 3,873,467 discloses a control composition for white blood cells using red blood cells stabilized by means of substituting for the blood plasma, a stabilizing media and fixed swollen red blood cells having increased mean cell volume to substitute for all of the leukocytes present. With swelling to approximately 50% greater volume, the specific gravity of the cell is reduced to be in the range of 1.06 to 1.08.

In the present invention, fixed human red blood cells substitute only for the smaller lymphocyte portion of the white blood cells, and there is commingled with these simulated lymphocytes, larger fixed animal red blood cells, representing the two larger sizes of the white blood cells, namely the mononuclear cells and the granulocytes. In this manner all three populations of the white blood cells are identified. In all instances, the red blood cells from three species of vertebrates are fixed so that they will not be lysed when determining the white blood cell parameters in the same blood control sample. In addition, the count for each of the three populations may be varied in proportion to one another without effecting a major shift in the original volume distribution.

The primary methods in this invention for controlling the size of the lymphocyte analogues are proper selection of the size of the non-fixed human red blood cells, the osmolality of the fixing solution and the variation in fixation temperature. Shrinking or expansion of the cells by manipulating their osmotic environment prior to fixation has limitations due to criticality of the fixation process required to maintain stability of the altered cells during the lysing of the untreated human red blood cells in the mixture.

Also, it is necessary to treat such red blood cells in a manner which allows them to be shrunken or swollen without excessive cell association or hemolysis to approximate the size needed.

The present invention embodies a composition prepared by mixing a suspension of fixed human red blood cells to simulate human lymphocytes, fixed red blood cells from turkeys to simulate human mononuclear cells, and a suspension of stabilized red blood cells from nurse sharks to simulate human granulocytes, all assembled in a liquid media and in such proportions as to provide a single composition to simulate human white cells (See FIG. 1B). This leukocyte analogue composition is then comingled with human red blood cells to be lysed, and stabilized platelets or platelet analogues to provide a single multiple-analysis reference control. The ratio of the simulated white blood cell population can be adjusted to represent abnormal low, normal and abnormal high conditions without affecting the size distribution of each type of simulated white blood cell. Modification of the preparative steps will allow the production of particles which represent different types of white blood cells which are characteristic of abnormal human white blood cell conditions.

In a preferred embodiment of this invention, the media is prepared according to the teachings of U.S. Pat. Nos. 4,299,726 and 4,358,394; and the platelets are stabilized according to any one of the methods described in U.S. Pat. Nos. 4,264,470, 4,389,490, or 4,405,719; all of these patents are assigned to Coulter Electronics, Inc.

This invention includes the selection and specific treatment steps for red blood cells from one or more animal sources. Generally, it is not possible to shrink or swell red blood cells more than about 30% to 50% total. Therefore, it is necessary to start with cells which approximate each population as shown in FIGS. 1A and 1B. The essence of the present invention lies in the discovery that red blood cells from the sources stated above have suitable characteristics to allow them to be shrunken or swollen and fixed without excessive cell association and hemolysis to approximate the size of the corresponding human blood cell with a narrow range of mean cell volume.

In the collecting step, the red blood cells are suspended in an anticoagulant, such as an alkali metal salt of ethylenediaminetetraacetic acid (EDTA) dissolved in a physiological saline solution (sodium chloride). It is envisioned that other anticoagulants and salts will do, as long as they do not cause undue hemolysis or cell association.

With regard to EDTA, we have discovered that the anticoagulant will affect the size of the blood cell as a function of concentration and the time of exposure. For example, cells suspended in 2.5 mM to 10 mM EDTA will retain the same size for up to 24 hours after collection. At a concentration greater than 10 mM EDTA, for example 20 mM, the cells will begin to swell in less than 24 hours. After 24 hours, the size of the cell increases with the concentration of EDTA as well as the exposure time. The maintenance or increase in cell size as a function of EDTA concentration and time of exposure, can be preserved by fixation. It is assumed that EDTA can significantly disrupt cell membrane structure and this disruption becomes magnified as a function of time. Thus, it is possible to manipulate cell size by controlling the concentration of anticoagulant and time of exposure prior to fixation.

In order to use universal preparative procedures for all white blood cell analogue populations, it is preferred to use red blood cells which must be shrunk prior to fixation. At the time of fixation, it is important to maintain hypertonicity to prevent any swelling of the cells. The effective final concentration of the salt solution should be in a range which is equal to and up to four times greater than that of normal serum, depending on the degree of shrinking required to simulate a specific white blood cell population. The addition of a fixing agent adds to the tonicity (osmolality) of the fixing solution.

Fixing of the shrunken cells is important to toughen the cell membranes and to prevent biodegradation of the membranes. This is accomplished by contacting the suspension of the cells with a solution of an organic aldehyde, including monoaldehydes such as formaldehyde, or dialdehydes such as glutaraldehyde. Glutaraldehyde is the preferred aldehyde, since it reacts more speedily than formaldehyde. Glutaraldehyde can be added in higher concentrations than the final concentration, so long as the final concentration thereof is in the range of about 0.1% to 1.0%. In accordance with the above value range example, but using formaldehyde in place of glutaraldehyde, the final concentration of formaldehyde is 2.5% to 10%; the preferred concentration is 5%. The only practical limitations on selection of an appropriate aldehyde and concentration thereof are elimination of undue cell association and hemolysis and potential undesirable electrolytic effects. The specific conditions recommended for each of the leukocyte components are given in each of the examples subsequently set forth.

It has been discovered that the smallest size of red blood cells with the narrowest distribution width are obtained with any kind of blood using fresh cells, or cells aged for not more than four days after phlebotomy, with a low concentration of the anticoagulant, used for collecting the fresh blood. A higher concentration of EDTA will result in larger non-fixed as well as fixed cells, which might not fit the criteria for the particular size range sought.

In a preferred embodiment, the blood cells are added to a chilled hypertonic salt solution containing glutaraldehyde. The reduced temperature has been shown to provide a qualitatively different cell as measured on a sizing apparatus such as a COULTER COUNTER analyzer. A qualitative difference includes a lower mean cell volume compared to fixing at room temperature. This difference, however, might not be evident until treatment of the fixed cell with a lysing agent as LYSE S ® II reagent in ISOTON ® II diluent. LYSE S and ISOTON are U.S. Registered Trademarks of Coulter Electronics, Inc.

After fixation, the cells are allowed to settle by gravity, are separated from the liquid phase, then are washed with a phosphate buffered saline solution and placed in a storage solution.

Since all three of the leukocyte components are to be combined into a single reference control for use with the known lysing agent for the red blood cells, the formulation for the diluent is the same for measuring all three components of the leukocyte analogue. The preferred formula for this diluent, as well as the formula for the lysing agent to be used for lysing the untreated red blood cells to be added later to the white blood cell assembly, are given below:

| | PREFERRED | RANGE |
|---|---|---|
| DILUENT | | |
| 1. Procaine hydrochloride | 0.11 g/L | 0.05 to 0.25 g/L |
| 2. N-(2-acetamido)iminodiacetic acid (ADA) | 1.40 g/L | 1.0 to 2.5 g/L |
| 3. Dimethylolurea | 1.0 g/L | 0.5 to 2.5 g/L |
| 4. q.s. to 1 liter with distilled water | | |
| LYSING AGENT | | |
| 1. Dodecyltrimethylammonium chloride-50% solution | 35 g/L | 20 to 55 g/L |
| 2. Tetradecyltrimethylammonium bromide | 3.7 g/L | 2 to 6 g/L |
| 3. Potassium cyanide | 300 mg/L | 125 to 1250 mg/L |
| 4. q.s. to 1 liter with distilled water | | |

The media for the hematological reference controls having stability up to six months includes lactose, fungicides and antibiotics, and supplementary agents such as purine nucleosides, bile salt, and cholic acid derivatives, phenothiazine compounds and the salts thereof having antihistamine properties, and 4-aminobenzoic acid esters and derivatives and their salts having anesthetic properties, or combinations thereof. Such media is more fully described in U.S. Pat. Nos. 4,213,876; 4,299,726; and 4,358,394.

The following specific example is disclosed in U.S. Pat. No. 4,299,726:

| Stabilizing Media for Conferring Long Term Stability on Red Blood Cells-Preferred Formulation, | |
|---|---|
| Approximate Amounts | Liter Formulation |
| 1. Distilled water | 500. ml |
| 2. Propyl paraben | 0.3 to 1.0 gm |
| 3. Methyl paraben | 0.5 to 1.0 gm |
| 4. Procaine hydrochloride | 0.1 to 0.5 gm |
| 5. Deoxycholic acid | 0.1 to 0.9 gm |
| 6. Lactose | 10.0 to 50.0 gm |
| 7. Actidione | 0.1 to 0.6 gm |
| 8. Trisodium citrate dehydrate | 3.0 to 8.0 gm |
| 9. Citric acid monohydrate | 0.3 to 0.9 gm |
| 10. Sodium dihydrogen phosphate monohydrate | 0.8 to 2.5 gm |
| 11. Phenergan hydrochloride | 0.1 to 1.0 gm |
| 12. Colistimethate, sodium | 0.2 to 0.9 gm |
| 13. Penicillin G., sodium | 0.5 to $\times 10^6$ $-3 \times 10^6$ units |
| 14. Kanamycin sulfate | 0.2 to 0.8 gm |
| 15. Neomycin sulfate | 0.2 to 1.0 gm |
| 16. 5'-AMP | 0.4 to 1.0 gm |
| 17. Adenine | 0.2 to 0.8 gm |
| 18. Inosine | 0.4 to 1.0 gm |
| 19. Dihydrostreptomycin sulfate | 0.2 to 1.0 gm |
| 20. Tetracycline hydrochloride | 0.2 to 1.0 gm |
| 21. 30% Bovine albumin | 100–350 ml |
| 22. q.s. to 1 liter with distilled water | |

For preparing the lymphocyte analogue, human erythrocytes are fixed with glutaraldehyde, following the procedure detailed below in Example 1, and then included in a predetermined amount in reference controls and calibrators, together with the mononuclear cell analogue (Example 2) and the granulocyte analogue (Example 3), or in whole blood controls containing, in addition to the lymphocyte analogues, washed red blood cells, or washed red blood cells and platelets.

Fresh human red blood cells must be washed to remove donor specific plasma proteins. This will reduce the probability of cell agglutination when mixing red cells from multiple blood cell donors.

Although most fixation occurs within two hours, more time is required for the red blood cells to be totally resistant to the usual red blood cell lytic agents employed in COULTER COUNTER automated hematology instruments. With careful selection of the human red blood cells and their dilution in a standard phosphate buffered solution, the length of time for fixation with glutaraldehyde will be optimal between 48 and 72 hours. Less than 48 hours of fixation may result in a partially fixed red blood cell with a mean cell volume less than that for a normal human lymphocyte. Partial fixation can be determined by detecting a shift to the left (drop in cell volume) in a partially fixed population after the addition of 10% by volume of LYSE S II reagent in ISOTON II diluent. The addition of a lytic agent to a diluent designed for the Model S Plus COULTER COUNTER series (e.g. Model S Plus II, III, and IV) will show similar results. The formulation for these diluents and lysing agents are disclosed hereinafter. A totally fixed human red blood cell (e.g. 48 hour fixation) shows a slight or no shift to the left (i.e. decrease in apparent volume) in the particle size distribution. Overfixation of red blood cells with glutaraldehyde is noted after 72 to 96 hours by a drop in particle size which is independent of the effect of above mentioned red blood cell lytic agents on 48 hour fixed human red blood cells. The desired amount of fixation will produce cells which are counted in the range of about 35 to 90±3 fL using a COULTER COUNTER Model S Plus type analyzer.

Human mononuclear cells are leukocytes which are intermediate in size between lymphocytes and granulocytes, and are counted in the size range, or monocyte region of between 90 and 160±3 fL. These cells are larger than fixed human red blood cells.

Arian red blood cells are larger than fixed human red blood cells, and close to the size of human mononuclear cells. For the purpose of this invention it has been found that fowl red blood cells such as goose, chicken, duck, and preferably turkey red blood cells, closely match the size and shape of human mononuclear cells, and lend themselves to the aldehyde stabilization process. These stabilized "simulated" monocyte cells provide a satisfactory substitute for human mononuclear cells in our control composition.

A process for preparing a mononuclear cell analogue from turkey red blood cells is detailed in Example 2.

Human granulocytes represent the largest size of the three leukocyte populations now counted by the COULTER COUNTER Model S Plus automated cell counter. The granulocytes are counted in the size range between about 160 and 450±3 fL.

It has now been discovered that proper treatment of the red blood cells of the nurse shark (Ginglymostoma cirratum) results in a size similar to human granulocytes. These erythrocytes generally show excellent suspension stability, highly reproducible volume distribution characteristics and are available on a commercial scale. When fixed with a cross-linking agent such as glutaraldehyde these erythrocytes will be electronically similar to the human granulocyte white blood cells.

Other non-human vertebrates which are known to have red blood cells in the desired size range for human granulocytes include other fishes, particularly members of the shark family and reptiles such as alligators. All of these non-human vertebrates have nucleated red blood cells which could be used. However, considerations, such as availability in quantity at reasonable expense, must be considered. Red blood cells of the nurse shark are readily available in quantity. The red blood cells of alligators tend to be less readily available, because alligators are presently a "protected" species by government authorities.

The cells of both alligators and nurse sharks are nucleated, but the presence of a nucleus is not essential for their use as a substitute for human white blood cells for the purposes of this invention. The presence of the nucleus in the shark red blood cell is not detrimental, inasmuch as the cells are stabilized with a cross-linking agent, such as glutaraldehyde, which prevents the cell membrane and cytoplasm from being stripped from the nucleus during lysis. The principle of differential analysis of fresh human white blood cells is based in part on the time of cytoplasmic membrane destruction, which is specific for each type of white blood cell population.

Shrinking or expanding of red blood cells by manipulating their osmotic environment prior to fixation has limitations due to criticality of the fixation process required to maintain stability of the altered cells. Generally, one cannot shrink or swell erythrocytes more than about 30% to 50% for this purpose. Therefore, it is necessary to start with animal erythrocytes which are close in size to what will be needed finally for use as a human granulocyte surrogate.

The usefulness of nurse shark erythrocytes as surrogate human granulocytes is limited by the necessity to shrink them to within the granulocyte size range. Exposure of erythrocytes to hypo- or hyperosmotic environments has the principal effect of changing the mean corpuscular volume, slightly increasing or decreasing the widths of the size distribution histograms, but causing only a trivial effect on symmetry of the size distribution histogram.

A standardized and stabilized red blood cell composition from the nurse shark provides a suitable reference control which is useful in the enumeration of human granulocytes by automated means using instruments operating under the Coulter principle, or by various microscopic techniques, such as illumination or phase contrast methods.

In accordance with this invention, nurse shark erythrocytes are altered and stabilized to simulate a human granulocyte analogue with respect to volume in femtoliters (fL) and count as $1 \times 10^3$ per microliter (uL). These fixed shark cells are stable for more than four months, based on volume distribution and count. The product is designed to behave in a manner which as closely as possible simulates fresh human granulocytes. In addition, the product is designed to possess a feature not found in fresh normal granulocytes, that is a high level of stability of the parameters measured by the cell counters in which it is used.

Example 3 is a specific example of preferred reagents and techniques for treating the shark cells, it being understood that the formulations are only illustrative. The reagents and/or techniques described can also be applicable to red blood cells from animals other than sharks. Other ingredients and proportions can be employed, in accordance with this disclosure. However, the size of the cell in a non-lytic solution, as in a buffer, may not visually show the entire effect of the treatment employed in this invention. The process requires the control of:

1. the concentration of the anticoagulant when collecting the blood cells;
2. the age of the anticoagulated non-fixed cells;
3. the concentration of cells during fixation;

4. the osmolality of the fixing solution;
5. the temperature of the fixing solution; and
6. the time of exposure to a cold hyperosmotic solution prior to fixation.

It has been discovered that the smallest size of red blood cells with the narrowest distribution width are obtained using fresh cells, or cells aged for not more than four days after phlebotomy, with a low concentration of EDTA. Using a higher concentration of EDTA on cells aged more than 24 hours will result in larger non-fixed as well as fixed cells which might not fit the 160 to 450±3 femtoliter criteria for human granulocytes.

Maintaining the fixing solution at 0° to 10° C., preferably 4° C., prior to and after the addition of chilled anticoagulated blood also will result in a smaller blood cell for use in this invention.

Nurse shark cells treated by the above method are highly stable when used in the reference control composition of this invention.

The simulated granulocytes can be used in a stand alone granulocyte control, or in a composite and unitary control standard which measures other blood parameters. More particularly, this novel granulocyte control is used in combination with compatible controls for other leukocyte components such as lymphocytes and mononuclear cells, to furnish a leukocyte control, which in turn is used in combination with reference controls for red blood cells and platelet parameters.

The following Examples 1 to 3 give detailed instructions for one method of preparing each of the three components of the leukocyte reference control. Example 4 shows an assembly of the three leukocyte populations. These procedures are controlled carefully throughout in order to make sure that the cells are not damaged and that the fixed cells become substantially totally resistant to the usual red blood cell lytic reagent. It will be understood that the formulations are only illustrative, and other ingredients and proportions may be employed, in accordance with this disclosure.

EXAMPLE 1

Lymphocyte Analogue from Human Red Blood Cells

The following is a specific example of preferred reagents and recommended specific procedural steps for treating human red blood cells to obtain a normal sized lymphocyte analogue. It will be understood that the formulations and the procedures only are illustrative and that other ingredients, proportions and procedures can be employed, in accordance with the disclosures in this invention.

Anticoagulants for Collection of Whole Blood

One or more of the following anticoagulants can be used, as determined by those skilled in the art.
1. Standard ACD (acid-citrate-dextrose)
2. Standard CPD (citrate-phosphate-dextrose)
3. Disodium EDTA (ethylenediamine tetraacetate), 2 mg/ml of blood.

STABILIZING MEDIA (LITER FORMULATION), as above set forth and with reference to U.S. Pat. No. 4,299,726.

FRESH BLOOD WASH SOLUTION AND WASHING AND RESUSPENDING SOLUTION FOR FIXED CELLS (WRS) (PHOSPHATE BUFFERED SALINE - LITER FORMULATION)

-continued

| 1. Sodium phosphate monobasic | 0.2 g |
| 2. Sodium phosphate dibasic .7H$_2$O | 2.0 g |
| 3. Sodium azide | 0.1 g |
| 4. Sodium chloride | 9.4 g |
| 5. q.s. to 1 liter with distilled water pH 7.3 to 7.5 osmolality 320 to 340 mOsm/kg. | |

ERYTHROCYTE DILUTING SOLUTION

| 1. Sodium chloride | 6.96 g |
| 2. Potassium chloride | 0.30 g |
| 3. Sodium phosphate monobasic | 1.31 g |
| 4. Sodium phosphate dibasic .7H$_2$O | 10.85 g |
| 5. q.s. to 1 liter with distilled water pH 7.3 to 7.5 osmolality 320 to 340 mOsm/kg. | |

Procedure

1. Select human red blood cells having a mean cell volume range of about 81 to 89 fL and red cell distribution width of less than 18 fL. Wash the packed human red blood cells with the Fresh Blood Wash Solution.

2. Dilute the washed packed cells with the Erythrocyte Diluting Solution to a count of $1 \times 10^6$/uL.

3. Prepare a glutaraldehyde fixative reagent having a glutaraldehyde content of about 1.0% to 10% by adding a commercial 25% glutaraldehyde product to the Erythrocyte Diluting Solution. The preferred concentration is 5%.

4. Add a measured amount of the fixative of step 3 to the washed red blood cell suspension to obtain a final glutaraldehyde concentration of 0.1% to 1.0%., and mix for about 20 minutes. Transfer to sealed containers which are rolled slowly for 12 to 72 hours.

5. Centrifuge the fixed cells at about 400 RCF for about 5 minutes. Remove the supernatent fluid, wash cells several times with the Fresh Blood Wash Solution (WRS), then resuspend in the Washing and Resuspending Solution (WRS).

6. Determine the mean cell volume to make certain that fixation is complete. Partial fixation will show a drop in volume after the addition of 10% LYSE S II reagent in ISOTON II diluent as previously described. A totally fixed red blood cell shows less than a 5 fL change in apparent volume.

7. For a stand alone lymphocyte control, resuspend the washed fixed cells in the resuspending solution and adjust the concentration to simulate that of human lymphocytes in normal human blood.

8. For multiple hemotological controls, resuspend the washed fixed cells in the media for the multiple parameter hematology control, the cell count being appropriate to measure lymphocytes.

9. The fixed cells can be stored for a time period of up to about six months.

In accordance with the above example, but using formaldehyde in place of glutaraldehyde, the final concentration of formaldehyde is 2.5% to 10%. The time required for fixation with formaldehyde is longer than with glutaraldehyde.

In accordance with the above example, but starting with other types of mammalian red blood cells, comparable results are obtained.

EXAMPLE 2

Mononuclear Cell Analogue from Turkey Red Blood Cells

The following is a specific example of preferred reagents and recommended specific procedural steps for treating turkey red blood cells to obtain the mononuclear cell analogue. It is understood that the leukocytes which are classified and counted in the above designated range as mononuclear cells includes monocytes. It will be understood that the formulations and the procedures are only illustrative and that other ingredients, proportions and procedures may be employed, in accordance with the disclosures in this invention.

Anticoagulants for Collection of Whole Blood

One or more of the following anticoagulants can be used in suitable quantity, as determined by one skilled in the art.
1. Standard ACD (acid-citrate-dextrose)
2. Standard CPD (citrate-phosphate-dextrose)
3. Disodium EDTA (ethylenediamine tetraacetate), 2 mg/ml of blood.

STABILIZING MEDIA (LITER FORMULATION), as above set forth and with reference to U.S. Pat. No. 4,299,726.

| TURKEY ERYTHROCYTE WASHING AND DILUTING SOLUTION(TEWDS)(LITER FORMULATION) | |
|---|---|
| 1. Sodium phosphate monobasic | 1.31 g |
| 2. Sodium phosphate dibasic | 10.35 g |
| 3. Sodium chloride | 2.50 g |
| 4. Potassium chloride | 0.3 g |
| 5. q.s. to 1 liter with distilled water pH 7.3 ± 0.1 osmolality 200 ± 10 mOsm/kg. | |

WASHING AND RESUSPENDING SOLUTION FOR FIXED CELLS (WRS), as set forth in Example 1.

Procedure

1. Centrifuge turkey fresh whole blood at 700 RCF for 10 minutes at ambient temperature. Remove the supernatent along with the buffy coat, being careful not to disturb the packed red blood cells.

2. Wash turkey red blood cells two times with 4 to 10 volumes of Turkey Erythrocyte Washing and Diluting Solution (TEWDS).

3. Dilute with Turkey Erythrocyte Washing and Diluting Solution (TEWDS) and measure out a 2 ml sample for determination of red blood cell count ($0.33 \times 10^6$/uL) and mean cell volume (approximately 155 fL) evaluation.

4. Prepare a glutaraldehyde fixing reagent having a glutaraldehyde content of about 1.0 to 10.0% by adding a commercial 25% glutaraldehyde product to the Turkey Erythrocyte Washing and Diluting Solution (TEWDS). The preferred concentration is 5%.

5. Add 1 volume of 1.0 to 10.0% glutaraldehyde fixative solution to 9 volumes of the washed red cell suspension, and mix thoroughly for about 3 to 4 minutes. Transfer to sealed containers which are rolled slowly for 20 to 28 hours.

6. Centrifuge the fixed cells at about 400 RCF for 5 minutes. Remove the supernatent fluid and wash several times with the wash solution (WRS).

7. For a stand alone mononuclear cell control, resuspend the washed fixed cells in the resuspending solution and adjust the concentration to simulate the number of mononuclear cells in normal human blood.

8. For multiple hemotological controls resuspend the washed fixed cells in the stabilizing media, as above set forth, for the multiple control in the appropriate concentration to measure mononuclear cells.

9. The fixed cells can be stored for a time period of up to about six months.

EXAMPLE 3

Granulocyte Analogue from Red Blood Cells of the Nurse Shark

The following is a specific example of preferred reagents and recommended specific procedural steps for treating red blood cells of the nurse shark (Ginglymostoma cirratum) to obtain the granulocyte analogue. It will be understood that the formulations and the procedures are only illustrative, and that other ingredients, proportions and procedures may be employed, in accordance with the disclosures in this invention.

| ANTICOAGULANTS FOR COLLECTION OF WHOLE BLOOD (LITER FORMULATION) | |
|---|---|
| 1. Disodium EDTA (ethylenediamine tetraacetate) | 16.8 g |
| 2. Sodium chloride | 17 g |
| 3. Urea | 21 g |
| 4. q.s. to 1 liter with distilled water | |

The shark ordinarily has a high concentration of urea in its blood which helps to maintain osmotic equilibrium of the red blood cells. For this reason urea is added to the subassembly in order to mimic the resulting osmotic conditions.

STABILIZING MEDIA (LITER FORMULATION), as above set forth.

WASHING AND RESUSPENDING SOLUTION FOR FIXED CELLS (WRS), as above set forth.

| SHARK CELL FIXING SOLUTION (LITER FORMULATION) | |
|---|---|
| 1. Sodium chloride | 100 g |
| 2. q.s. to 1 liter with distilled water | |
| 3. Osmolality 3000 ± 100 mOsm/kg | |
| FINAL FIXING REAGENT (LITER FORMULATION) | |
| 1. Shark fixing solution | 0.940 L |
| 2. Glutaraldehyde 25% solution | 0.040 L |
| 3. Packed shark red blood cells | 0.020 L |

Procedure

1. Collect fresh whole blood from a nurse shark in an ethylenediamine tetraacetic acid (EDTA) anticoagulant solution having a final concentration of 2.5 to 30 mM (typically 5 mM). This is a filtered EDTA solution having an osmolality of 1030±30 mOsm/kg and a pH of 7.0±1.

2. Centrifuge the anticoagulated whole blood mixture within 24 hours of phlebotomy; remove the supernatant fluid and the buffy coat containing the white blood cells, being careful not to disturb the packed red blood cells. The glutaraldehyde fixation processing of blood can take place within four days if it is stored in less than 20 mM EDTA; and fixation can take place in less than one day if stored in 20 to 30 mM of EDTA.

3. Prepare and chill to about 0° to 10° C. a glutaraldehyde fixing solution which has a glutaraldehyde concentration of 1.0%, and an osmolatity of 1000 to 4000 mOs/kg (preferred concentration is 3000±100 mOs/kg). The pH range is 4.5 to 8; preferred pH is 4.0±0.5.

4. Centrifuge; within 60 minutes after centrifugation add the non-washed packed red blood cells, with mixing, to the chilled fixing solution (see Final Fixing Reagent) to give a glutaraldehyde concentration of 1.0%. Continue the fixing operation for a minimum of 6 hours at 0° to 10° C. and, if needed, for up to 48 hours.

5. Wash the fixed cells two or three times with approximately 5 volumes of phosphate buffered saline solution.

6. Store cells in the Washing and Resuspending Solution for a time period up to 60 days.

7. For a stand alone granulocyte control, resuspend the washed fixed cells in the resuspending solution, and adjust the cell concentration to simulate that of granulocytes in normal human blood.

8. For multiple hemotological controls, resuspend the washed fixed cells in the stabilizing media, as above set forth, for the multiple control in the appropriate concentration to measure granulocytes.

9. The fixed cells can be stored for a time period of up to about six months.

In accordance with the above procedure and techniques, but substituting for the shark red blood cells the red blood cells from other sources, similar results are obtained to give modified cells useful for other purposes in addition to simulate granulocytes.

EXAMPLE 4

In a sub-assembly for determining the total white blood cell content of a normal human blood sample, the following quantities of the individual components are employed:

|          |           |                          | Stock Solution        |
|----------|-----------|--------------------------|-----------------------|
| 0.0146 L | Example 1 | lymphocytes              | $3.5 \times 10^6$/uL  |
| 0.0105 L | Example 2 | mononuclear cells        | $1.8 \times 10^6$/uL  |
| 0.975 L  | Example 3 | granulocytes             | $0.4 \times 10^6$/uL  |
| 0.0004 L | diluent   | phosphate buffered saline|                       |

This sub-assembly can be stored for up to about six months.

It has been found that untreated human red blood cells, stabilized by suspension in media described earlier, can satisfactorily provide the red blood cell component of the subject composition. The untreated red blood cells are hemolyzed readily in the prior operational step for the white blood cell count and subsequent hemoglobin determination.

Suspensions of untreated human red blood cells, simulated white blood cells, and stabilized or simulated platelets are mixed in such proportion that the final red blood cell, white blood cell and platelet counts, as well as hemoglobin content and hematocrit fall in the range considered normal for human blood.

Stabilized platelets are furnished by methods known in the art. Useful methods include:

1. A combination of iodoacetamide and an iminodiacetlc acid or salt thereof, together with a compatible bacteriostatic agent in an aqueous solution which is maintained at a preselected range of pH and osmolality as is described in U.S. Pat. No. 4,405,719.

2. A fixative-stabilizing composition containing a glutaraldehyde concentration of 0.1% to 5% and a non-ionic surfactant which is a mixture of ethoxylates of certain isomeric linear alcohols, as is more fully described in U.S. Pat. No. 4,389,490.

3. A human platelet analogue comprising goat erythrocytes stabilized, combined and blended as necessary to have a size range and volume distribution close to that of human platelets, as is described in U.S. Pat. No. 4,264,470.

Where the platelets are used as controls for procedures that include unfixed red blood cells which are to be lysed, it is necessary to use fixed cells as a leukocyte analogue. These can be prepared, for example, by the method described in U.S. Pat. No. 4,179,398.

The values for each of the heretological parameters can be varied to represent abnormal low and abnormal high conditions. The white blood cell count in normal blood is 5,000 to 11,000 per microliter (uL) with a lymphocyte value of 20 to 40%, mononuclear cell value of less than 10% and a granulocyte value of 60 to 80%. The normal range in human blood for red blood cells is 4,000,000 to 5,000,000 cells per microliter. The normal hemoglobin value is 12 to 16 grams/100 ml. The term "hematocrit" is defined as the ratio of volume of packed red blood cells to the volume of whole blood. The normal ratio in humans is about 45%. The mean corpuscular volume is the ratio of the volume of packed red blood cells in ml per liter of blood to red blood cells in millions per microliter. The mean corpuscular hemoglobin concentration is an index indicating the mean or average weight of hemoglobin per 100 ml of packed red blood cells in terms of percent. The mean corpuscular hemoglobin is the ratio of hemoglobin content, in grams per liter, to red blood cells, in millions per microliter.

A control product must accurately indicate on a comparative basis what a test sample of fresh whole blood constitutes with regard to all the above determinations. It is evident how important it is for the control product to simulate normal human cells in an anticoagulant.

This invention primarily is directed to a hematology reference control solution, the white cell control portions thereof consisting of three types of fixed red blood cells of determined size distribution for checking the predetermined lower and upper threshold settings for each class or subclass of leukocytes, as set electrically in the particle analyzing instrument. The upper and lower electronic threshold setting for each of the classes of leukocytes are checked by the relationship of the particle counts of each of the discriminator regions compared to known values. Each type of simulated leukocyte must maintain size independent of total cell count and independent of its proportionality to one or more types of simulated leukocyte populations.

The cells treated by the method disclosed herein provide an excellent system of checks and balances so necessary in hematological determinations.

While in the foregoing specification, a detailed description of the invention has been set down for the purpose of illustration, many variations in the details herein given may be made by those skilled in the art without departing from the spirit and scope of the invention.

We claim:

1. A hematology reference control fluid suspension for use in an automatic cell counting and sizing instrument, said reference control comprising a predetermined number of treated red blood cells to be counted in each of at least two of the following approximate size ranges:

35 to 90±3 fL
90 to 160±3 fL
160 to 450±3 fL in a compatible aqueous and substantially isotonic stabilizing media; and said cells in each size range functioning as a substitute for one of three white cell sub-populations in human blood, said sub-populations being lymphocytes, monocytes or granulocytes.

2. The reference control of claim 1 wherein said treated red blood cells include those which have a volume which is measured by said instrument in the size range of 90 fL to 160±3 fL, are derived from fowl and function to simulate human mononuclear cells.

3. The reference control of claim 1 wherein said treated red blood cells include those which have a volume which is measured by said instrument in the size range of 160 to 450±3 fL, are derived from non-human verterbrates selected from the group consisting of reptiles and fish, and function to simulate human granulocytes.

4. The reference control of claim 3 wherein said reptiles are alligators (*Alligator mississipiensis*).

5. The reference control of claim 1 wherein said stabilizing media includes lactose, fungitides and antibiotics, and supplementary agents selected from the group consisting of purine nucleosides, bile salts and cholic acid derivatives, phenothiazine compounds and their salts having antihistamine properties, and 4-aminobenzoic acid ester derivatives and their salts having local anesthetic properties.

6. The reference control of claim 1 wherein said treated red blood cells include those which have a volume which is measured by said instrument in the size range of 160 to 450±3 fL, are derived from nurse sharks (*Ginglymostoma cirratum*), and function to simulate human granulocytes.

7. A hematology reference control fluid suspension for use with an automatic blood cell counting instrument, said reference control comprising a predetermined number of treated red blood cells which function to simulate human granulocytes and are derived from non-human vertebrates selected from the group consisting of reptiles, nurse sharks and-fish.

8. The reference control of claim 7 further including a predetermined number of treated red blood cells which function to simulate human mononuclear cells and are derived from fowl.

9. A hematology reference control comprising at least two distinct groups of simulated leukocytes, derived from treated red blood cells wherein each group of simulated leukocyte maintains size independent of total cell count and independent of its proportionality to one or more other groups of simulated leukocyte populations.

10. A stand alone hematology reference control fluid suspension for use with an automatic blood cell counting instrument, said reference control comprising a predetermined number of treated red blood cells of the nurse shark which function to simulate human granulocytes.

11. The reference control of claim 10 further including a predetermined number of treated red blood cells which function to simulate human mononuclear cells and are derived from turkeys.

12. A stand alone hematology reference control fluid suspension for use with an automatic blood cell counting instrument, said reference control comprising a predetermined number of treated red blood cells which function to simulate human mononuclear cells and are derived from turkeys.

* * * * *